United States Patent [19]

Stokdijk

[11] Patent Number: 5,675,517
[45] Date of Patent: Oct. 7, 1997

[54] FLUORESCENCE SPECTRAL OVERLAP COMPENSATION FOR HIGH SPEED FLOW CYTOMETRY SYSTEMS

[75] Inventor: Willem Stokdijk, Livermore, Calif.

[73] Assignee: Systemix, Palo Alto, Calif.

[21] Appl. No.: 428,720

[22] Filed: Apr. 25, 1995

[51] Int. Cl.[6] .................................................. G01C 25/00
[52] U.S. Cl. ........................... 364/571.01; 356/338
[58] Field of Search ........................ 364/571.01, 571.02, 364/555, 550; 327/307, 309; 356/349, 338, 340, 364, 441, 442, 39, 341, 342, 343, 335, 336, 432–437; 250/564, 565, 573

[56] References Cited

U.S. PATENT DOCUMENTS

| | | | |
|---|---|---|---|
| 3,699,336 | 10/1972 | Ehrlich et al. | 250/83.3 |
| 4,284,412 | 8/1981 | Hansen et al. | 23/230 B |
| 4,325,706 | 4/1982 | Gershman et al. | 23/230 B |
| 4,375,068 | 2/1983 | McBride | 358/111 |
| 4,481,597 | 11/1984 | Robbins | 364/604 |
| 4,661,913 | 4/1987 | Wu et al. | 364/500 |
| 4,764,013 | 8/1988 | Johnston | 356/349 |
| 4,775,833 | 10/1988 | Roos et al. | 324/71.1 |
| 4,857,451 | 8/1989 | Schwartz | 435/7 |
| 5,050,987 | 9/1991 | Kosaka | 356/73 |
| 5,150,313 | 9/1992 | van den Engh et al. | 364/569 |
| 5,351,118 | 9/1994 | Spinell | 356/72 |
| 5,504,337 | 4/1996 | Lakowicz et al. | 250/461.2 |

FOREIGN PATENT DOCUMENTS

| | | | |
|---|---|---|---|
| 0585754 | 3/1994 | European Pat. Off. | G01N 15/14 |
| 0641573 | 3/1995 | European Pat. Off. | A61N 1/39 |

OTHER PUBLICATIONS

Hiebert, R. D. "Electronics and Signal Processing", Flow Cytometry and Sorting, Second Edition, pp. 127–144, 1990 Wiley–Liss Inc.

Loken, Michael R., David R. Parks and Leonard A. Herzenberg "Two–Color Immunofluorescence using a Fluorescence–Activated Cell Sorter", The Journal of Histochemistry and Cytochemistry, vol. 25, No. 7, 1977, pp. 899–907.

Bagwell, C. Bruce and Earl G. Adams, "Fluorescence Spectral Overlap Compensation for Any Number of Flow Cytometry Parameters", Annals New York Academy of Sciences, pp. 167–184 date unknown.

Primary Examiner—James P. Trammell
Attorney, Agent, or Firm—Blakely, Sokoloff, Taylor & Zafman

[57] ABSTRACT

A fluorescence spectral overlap electronic compensation circuit for high speed flow cytometry systems is provided. In high-speed flow cytometry systems, such as systems with a pulse rise time up to 2 μs, baseline restoration circuits may not adequately eliminate the DC offset of input signals, in which case, DC offset will result in errors after overlap compensation. In addition, analog spectral overlap compensation operations may result in signal distortions that are unacceptable when using a log amp whose output signal depends on the absolute value of its input signal. The disclosed fluorescence spectral overlap compensation circuit includes an adjustable DC offset compensation circuit to more accurately reduce the DC offset components of signals, and a half-wave rectifier for eliminating the signal distortions caused by spectral overlap compensation operations.

21 Claims, 8 Drawing Sheets

FLUORESCENCE SPECTRAL OVERLAP COMPENSATION FOR HIGH SPEED FLOW CYTOMETRY SYSTEMS

FIELD OF THE INVENTION

The present invention relates to a flow cytometry system, and more specifically, to a method and apparatus for compensating for spectral overlap of fluorochrome emission.

BACKGROUND OF THE INVENTION

Flow cytometry involves serial characterizing of particles, such as cells or cellular components, in a fluid stream. The particles are tagged with, for example, a fluorescent dye. The stream of particles is then passed through a laser beam, causing the tag to fluoresce. The light pulses from the tag provide an identifying signature for the particle. The light pulses typically have pulse widths between three to five microseconds. A detector detects the pulses from the tag and transmits a signal representing the pulses to a data acquisition system (DAS). The DAS then categorizes the particles based on the detected pulses.

Some flow cytometry systems segregate particles based on their classification after the particles have been classified. This segregation is performed by causing the stream to break into droplets. Preferably, each droplet will contain one particle. As soon as the droplet is formed, the droplet is electrically charged responsive to the category to which the particle within the droplet belongs. The droplet then falls between electrostatic plates. Differently charged droplets will be pulled in different directions as they travel between the charged plates.

A multiple-laser flow cytometer uses a plurality of spaced beams, each of a different wavelength, to excite different fluorescent dyes. Thus, more information can be obtained using a multiple-laser flow cytometer since each particle can be probed successively by each beam to provide information relating to a multitude of characteristics.

Data collection in a multibeam system is complex, because particle classification involves the cross-correlation of information detected by two or more different sensors. In cytometer systems which segregate particles in real time, the data for a particle must be synchronized and the categorization operation completed between the time the particle passes a laser and the time the stream breaks into droplets.

One method for acquiring and synchronizing particle data at high speed in a multibeam system is disclosed in U.S. Pat. No. 5,150,313 issued to van den Engh et al. on Sep. 22, 1992. According to this method, analog signals from various detectors are immediately converted to digital data. The digital data generated by each detector in response to detecting a given particle is synchronized with the digital data from the other detectors for the given particle using FIFO buffers. The synchronized data for the given particle is then sent sequentially over a digital data bus to a computer.

As the data acquisition rate of cytometry systems increases, it becomes increasingly difficult to maintain the integrity of the data generated by the detectors. In many systems, the electrical current from the detectors varies in response to detected pulses from the particles. Therefore, as a first step, the current-encoded signal generated by each detector is processed by a current-to-voltage converter to produce a voltage-encoded pulse signal. Typically, only the peak of the signal is important. The resulting voltage-encoded pulse signal has an information-distorting DC component resulting in false values of peak signal.

Normally, this offset may be eliminated with a baseline restoration circuit. Baseline restoration circuits are circuits which reduce the DC voltage of an input signal based on an estimated DC component. Baseline restoration circuits are typically feedback circuits. Thus, the estimated DC level used to reduce the voltage of a voltage-encoded input signal is based on the level of the current-to-voltage converter's output signal.

Figure 1:
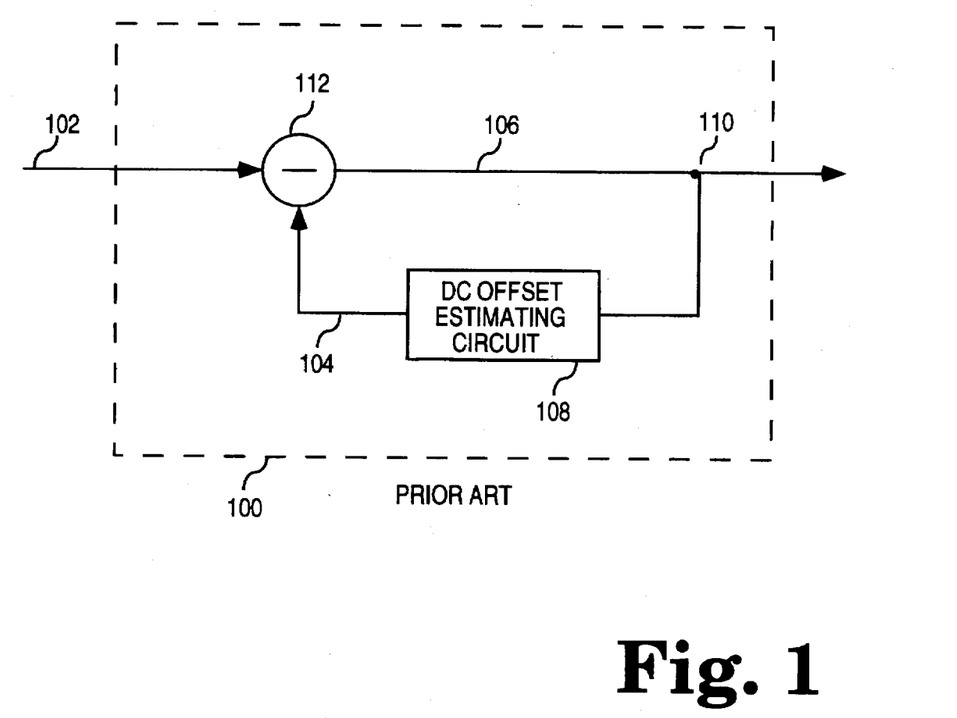
FIG. 1 illustrates a feedback circuit for reducing the DC component of a signal.

FIG. 1 illustrates a typical baseline restoration circuit 100. The input signal on an input line 102 is reduced based on an estimated DC component signal on a line 104 to produce a DC-compensated output signal on a line 106. The estimated DC component signal is produced by a DC component estimating circuit 108 based on the DC-compensated output signal on line 106 at junction 110.

The effectiveness of baseline restoration circuit 100 is reduced when data is acquired a higher frequencies. Specifically, at frequencies above approximately 5000 events/second and pulse rise times less than or equal to 2 microseconds, the magnitude of the DC-component still present in the DC-compensated output signal will typically be greater than 1 mV. A DC-component of that magnitude is typically unacceptable due to the sensitivity of the signal processing circuitry that receives the DC-compensated output signal. Specifically, the signal processing circuitry that follows a baseline restoration circuit in a flow cytometry system typically includes a logarithmic amplifier that is sensitive to input signals having amplitudes at or greater than 1 mV.

Often, the spectra of two dyes used simultaneously are likely to have an area or areas of overlap, called spectral overlap. The process by which the electronics adjusts for spectral overlap is called "compensation".

Increasing the data acquisition rate in a flow cytometry system may also result in information distortion during spectral overlap compensation operations. Spectral overlap compensation is typically performed to more clearly segregate data distributions acquired in multiple-detector flow cytometry systems into predefined quadrants.

Figure 2:
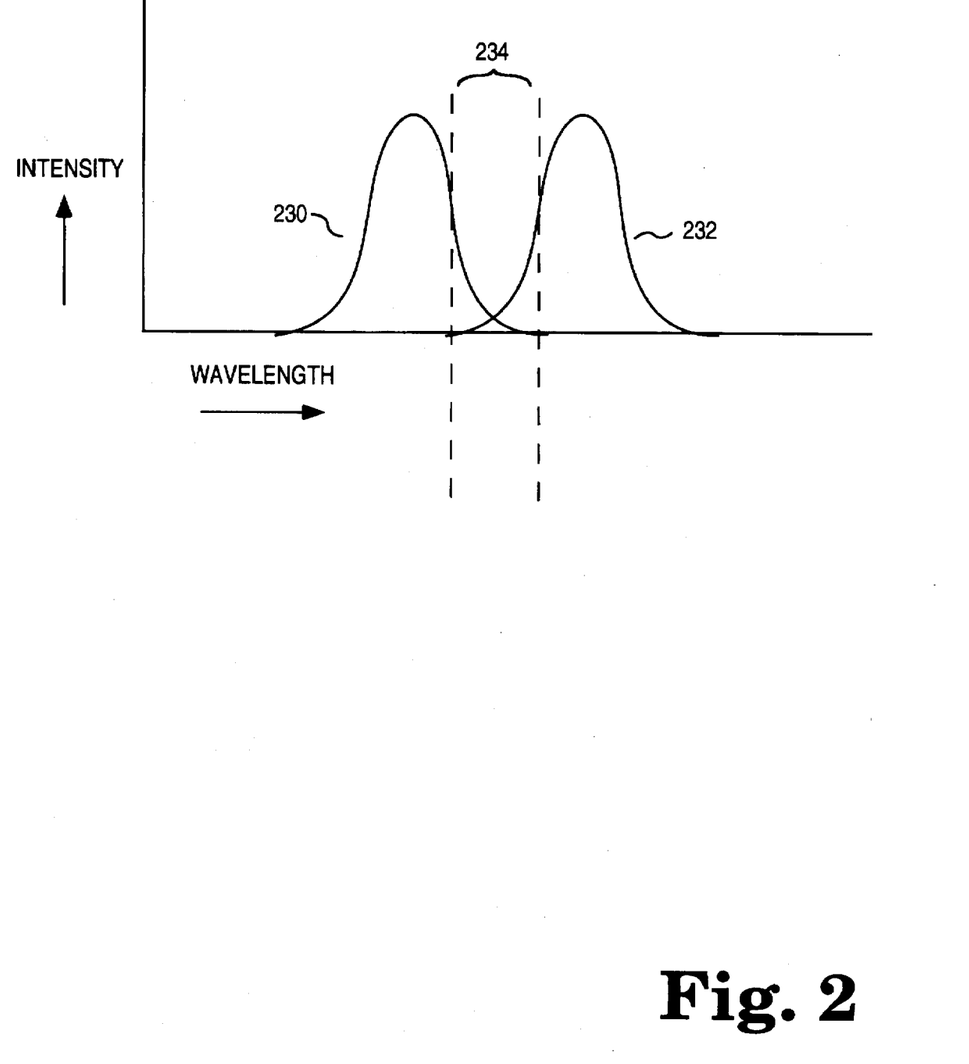
FIG. 2 illustrates the overlap of optical spectra of differently-tagged particles.

Referring to FIG. 2, detection of an X-tagged particle may result in a spectral response 230, while detection of a Y-tagged particle may result in a spectral response 232. Some particles will have both X and Y tags. There is a range of frequencies 234 at which both X and Y-tagged particles produce output signals. Because of this overlap, populations may not categorize squarely into categorization quadrants. However, categorization into quadrants is preferable for most sorting electronics and/or analysis software.

Most flow cytometry systems compensate for this overlap by reducing the signal of one detector by a percentage of a signal from another detector. This spectral overlap compensation process is described in the article "Two Color Immunofluorescence Using a Fluorescence-Activated Cell Sorter", Loken M R, Parks D R, Herzenberg L A, Journal of Histochem Cytochem, 25:899 (1977).

This spectral overlap compensation method works well for typical multiple detector flow cytometry systems. However, in systems with input pulse rise times at or less than 2 μs, it becomes increasingly difficult to precisely align the two detector-generated signals to accurately perform the required signal subtraction operation. Even small signal alignment errors may cause signal reduction errors, some of which may result in undershoot portions on the output signal. Such undershoot portions may significantly distort the information contained in the signal if they are amplified by a logarithmic amplifier, whose output signal depends on the absolute value of its input voltage.

Another approach to compensation is described in the paper: Fluorescence Spectral Overlap Compensation for Any Number of Flow Cytometry Parameters by C. Bruce Bagwell and Earl G. Adams, Annals New York Academy of Sciences, pg. 167–184 (1992). This approach is limited due to the relatively low resolution of analog/digital conversion in typical flow cytometers, and therefore is useful in a limited number of applications.

Based on the foregoing, it is clearly desirable to provide a method and apparatus for use in a high speed data acquisition system for reducing the DC component. It is further desirable to reduce the DC component which cannot be completely eliminated due to the limitations of feedback baseline restoration circuits. In addition, it would be desirable to reduce the information distortion which may result from signal alignment errors during spectral overlap compensation operations.

SUMMARY OF THE INVENTION

A preamplifier for use in a flow cytometry system is provided according to one aspect of the present invention. The preamplifier includes a baseline restoration circuit and an offset compensation circuit. The baseline restoration circuit is coupled to receive a voltage-encoded signal. The baseline restoration circuit generates an estimated DC component responsive to the voltage-encoded signal. The offset compensation circuit is coupled to the baseline restoration circuit. The offset compensation circuit generates an offset signal indicating a voltage offset. The preamplifier is configured to attenuate the voltage-encoded signal based on the voltage offset and the estimated DC component to produce a DC compensated signal.

A spectral overlap compensation system for use in a flow cytometry system is provided according to one aspect of the present invention. The spectral overlap compensation system includes an overlap compensation circuit, a half-wave rectifier and an amplifier. The overlap compensation circuit is coupled to a first detector. The overlap compensation circuit receives a first signal from the first detector. The overlap compensation circuit subtracts a second signal from the first signal to produce an overlap compensated signal. The second signal is based on signals produced by one or more other detectors. The half-wave rectifier is coupled to the overlap compensation circuit. The half-wave rectifier receives the overlap compensated signal and generates a rectified signal. The amplifier is coupled to the half-wave rectifier. The amplifier amplifies the rectified signal and generates an amplified signal.

The effect of the half-wave rectifier depends on the type of amplifier employed. For example, a logarithmic amplifier whose output depends on the absolute value of its input signal requires the half-wave rectifier to prevent false reading due to signal undershoots.

According to another aspect of the invention, a data acquisition system for use in a flow cytometry system is provided. The data acquisition system includes a detector, a preamplifier, an amplifier, an analog-to-digital converter and a computer.

The detector is disposed to detect particles having a first tag type. The detector generates an analog current which corresponds to detecting particles having the first tag type. The preamplifier is operatively coupled to the detector. The preamplifier receives the analog current from the detector. The preamplifier generates a signal based on the analog current and an estimated DC component of the signal. In a high-speed data acquisition system, a feedback baseline restoration circuit will tend to underestimate the DC component of a signal. Therefore, the preamplifier of the present invention reduces the DC component based on the sum of the estimated DC component and a predetermined offset.

The amplifier is operatively coupled to the preamplifier. The amplifier amplifies the DC compensated signal and generates an amplified signal. The analog-to-digital converter is operatively coupled to the amplifier. The analog-to-digital converter generates digital data responsive to the amplified signal. The computer is operatively coupled to the analog-to-digital converter. The computer categorizes the particles responsive to the digital data.

According to another aspect of the present invention, a data acquisition system for use in a multiple-detector flow cytometry system is provided. The data acquisition system includes a first detector, a second detector, a reduced signal transmission circuit, an overlap compensation circuit, a half-wave rectifier, an amplifier, an analog-to-digital converter and a computer.

The first detector is disposed to detect particles having a first tag type. The first detector generates a first analog current which corresponds to detecting particles having the first tag type. The second detector is disposed to detect particles having a second tag type. The second detector generates a second analog current which corresponds to detecting particles having the second tag type.

The reduced signal transmission circuit is operatively coupled to the second detector. The reduced signal transmission circuit receives the second analog current and generates a reduced level signal. The reduced level signal represents the second analog current reduced by a predetermined percentage. The overlap compensation circuit is operatively coupled to the first detector and the reduced signal transmission circuit. The overlap compensation circuit subtracts the reduced level signal from a first signal representative of the first analog current to produce an overlap compensated signal.

Due to timing and component imprecision, the overlap compensated signal produced by this subtraction operation may dip below ground. If these below-ground dips are not removed, they may result in erroneous signals after logarithmic amplification. Therefore, the overlap compensated signal is fed into the half-wave rectifier. The half-wave rectifier is operatively coupled to the overlap compensation circuit. The half-wave rectifier receives the overlap compensated signal and generates a rectified signal in which the below-ground signal dips have been eliminated.

The log amplifier is operatively coupled to the half-wave rectifier. The amplifier generates an amplified signal by amplifying the rectified signal. The analog-to-digital converter is operatively coupled to the amplifier. The analog-to-digital converter generates digital data responsive to the amplified signal. The particles are categorized responsive to the digital data.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENT

Figure 3:
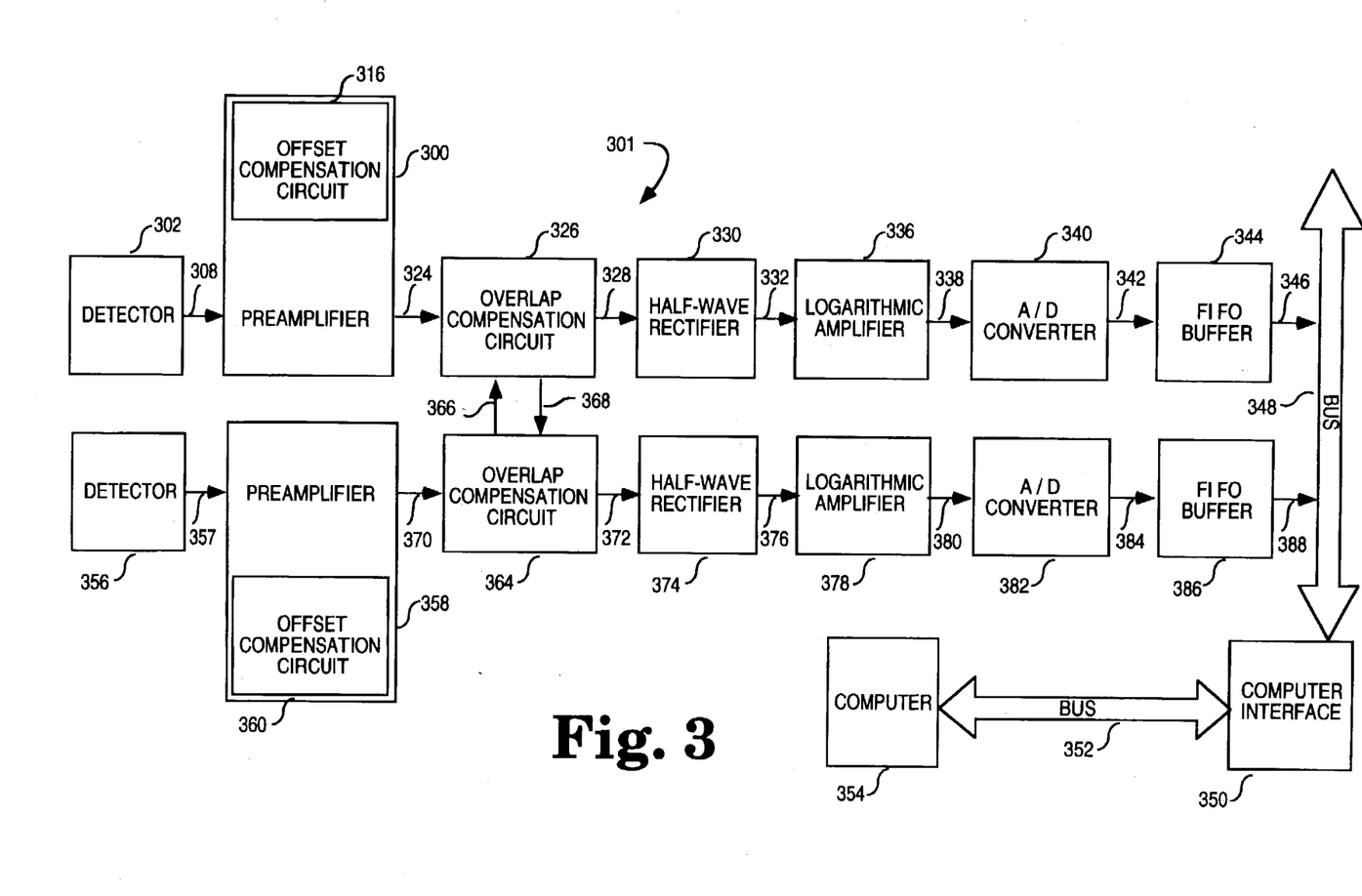
FIG. 3 is a block diagram illustrating the data acquisition portion of a multiple-detector flow cytometry system according to an embodiment of the invention.

Referring to FIG. 3, it illustrates a block diagram of a two parameter data acquisition system 301 for a multiple-detector flow cytometry system. Typical cytometry systems include five to eight detectors. However, for the purposes of explanation, data acquisition system 301 is illustrated with two detectors 302 and 356. Data acquisition system 301 also includes two preamplifiers 300 and 358, two overlap compensation circuits 326 and 364, two half-wave rectifiers 330 and 374, two logarithmic amplifiers 336 and 378, two analog-to-digital converters 340 and 382, and two digital first-in-first-out (FIFO) buffers 344 and 386. Data acquisition system 301 further includes a bus 348, a computer interface 350, a second bus 352, and a computer 354. Preferably, detector 302 is configured to detect particles (e.g. cells) with a first type of tag, and detector 356 is configured to detect particles with a second type of tag. For the purposes of explanation, it shall be assumed that detector 302 detects "X-tagged particles", while detector 356 detects "Y-tagged particles". Some particles may have both X and Y tags. Such particles will be detected by both detector 302 and detector 356.

Detector 302 is coupled to preamplifier 300 by a coaxial cable 308. Detector 302 generates a signal to preamplifier 300 over coaxial cable 308 indicative of the light detected from the X-tagged particles. The signal generated by detector 302 is current-encoded. That is, the current of the signal generated by detector 302 varies based on the light pulses detected by the detector 302.

Preamplifier 300 includes a current-to-voltage converter for converting the current-encoded signal to a voltage-encoded pulse signal, and a feedback baseline restoration circuit for reducing the DC component of the voltage-encoded pulse signal. However, as explained above, due to the high data acquisition rate of detector 302, the baseline restoration circuit within preamplifier 300 will not completely eliminate the DC component on the voltage-encoded pulse signal. Therefore, preamplifier 300 further includes an offset compensation circuit 316 to reduce the DC component that remains on the voltage-encoded pulse signal. The resulting DC compensated signal is sent over line 324 to overlap compensation circuit 326.

As described above, there may be an overlap between the optical spectra of particles with different tags. To provide a more discrete classification of the tagged particles, overlap compensation circuit 326 reduces the amplitude of the DC compensated signal on line 324 by a percentage of a DC compensated signal on line 370, which encodes information detected by detector 356. A signal representing a fraction of the DC compensated signal on line 370 is transmitted to overlap compensation circuit 326 by overlap compensation circuit 364 via a line 366.

Similarly, overlap compensation circuit 364 reduces the DC compensated signal on line 370 based on a signal generated by overlap compensation circuit 326 over a line 368. The signal generated over line 368 by overlap compensation circuit 326 has an amplitude equal to a fraction of the amplitude of the DC compensated signal on line 324.

As explained above, the spectral overlap compensation operation performed by overlap compensation circuit 326 may result in an output signal on line 328 which, at times, undershoots below zero-volts. For example, assume that during a particular time period line 324 carries the signal 802 shown in FIG. 8, and line 370 carries the signal 804 shown in FIG. 8. To compensate for spectral overlap, overlap compensation circuit 326 subtracts a fraction (e.g. 30%) of signal 804 from signal 802. Due to circuit imprecision, the resulting signal in high speed systems may have negative undershoots, as shown in signal 806. These negative undershoots are caused by timing and component imprecision in a high-speed system. If not eliminated, these negative undershoots will distort the actual measurements and result in positive, amplified spikes 812 when the overlap-compensated signal is log amplified through logarithmic amplifier 336, which has an output that depends on the absolute value of its input signal.

Figure 8:
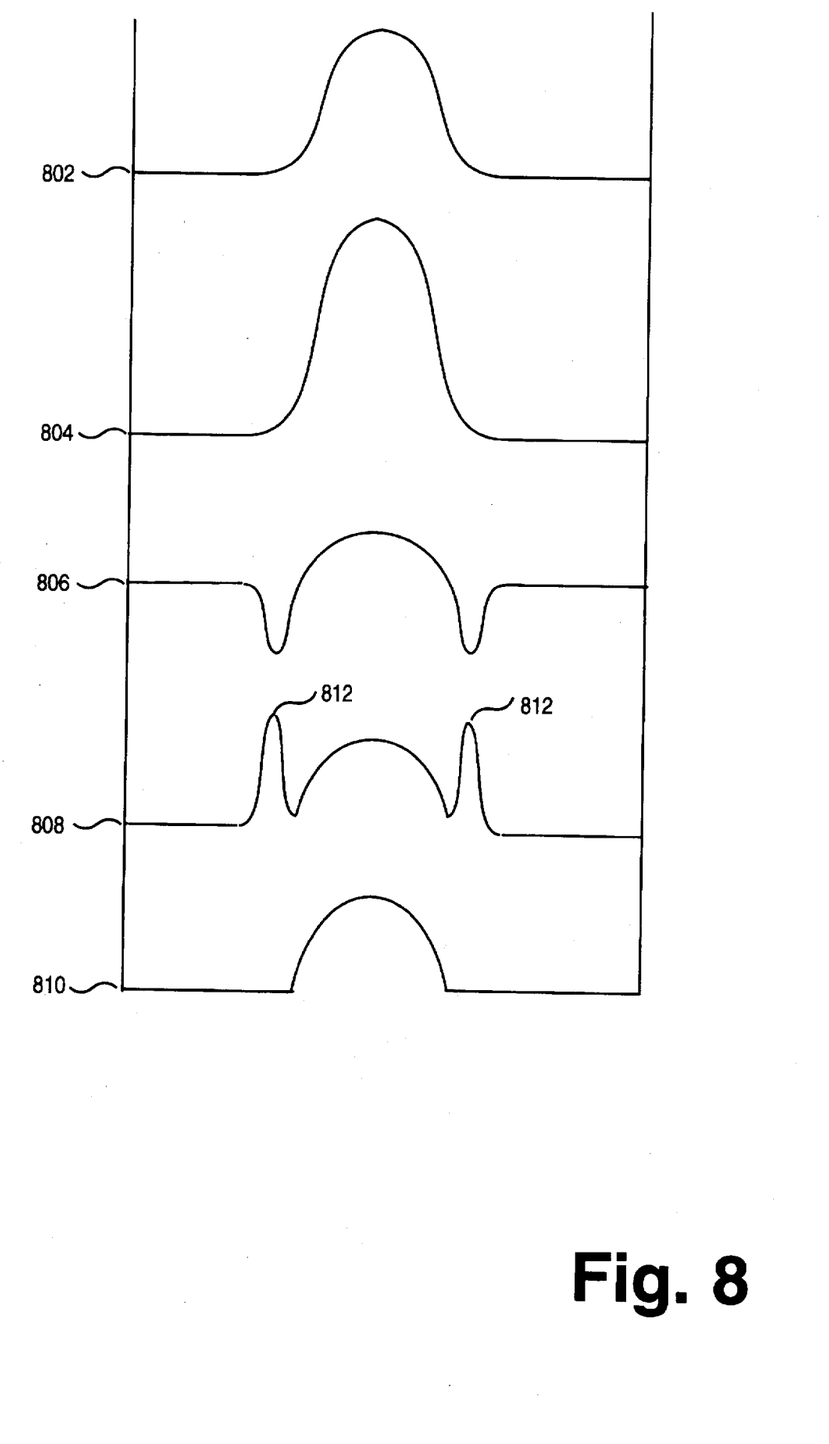
FIG. 8 illustrates exemplary signals within the data acquisition portion of the multiple-detector flow cytometry system illustrated in FIG. 3.

These undershoots are reduced by passing the overlap-compensated signal through half-wave rectifier 330 before sending the signal to logarithmic amplifier 336. Half-wave rectifier 330 receives the signal 806 over line 328 and eliminates undershoot portions of the signal. The resulting rectified signal is then passed to logarithmic amplifier 336 over line 332 to produce an amplified signal 810.

Logarithmic amplifier 336 amplifies the rectified signal and sends the resulting amplified signal to analog-to-digital converter 340 over line 338. Analog-to-digital converter 340 converts the amplified signal on line 338 to a digital signal and transmits the digital signals over line 342 to FIFO buffer 344. FIFO buffer 344 receives the digital signals on line 342 and transmits the digital data contained in the signal to computer 354 over buses 348 and 352 through computer interface 350. FIFO buffer 344 aligns the digital data contained therein with the digital data stored in FIFO buffer 386 so that data corresponding to the same particle but detected by different detectors is sent to bus 348 sequentially by FIFO buffer 344 and FIFO buffer 386.

In a particle-sorting flow cytometry system, each particle is categorized based on the data received from data acquisition system 301. Each particle is then electrically charged and segregated based on the category of the particle.

Detector 356 is coupled to preamplifier 358 by a line 357. Preamplifier 358 includes an offset compensation circuit 360. Overlap compensation circuit 364 is coupled to preamplifier 358 by a line 370, to overlap compensation circuit 326 by line 366 and 368, and to half-wave rectifier 374 by a line 372. Logarithmic amplifier 378 is coupled to half-wave rectifier by a line 376, to analog-to-digital converter 382 by a line 380. FIFO buffer 386 is coupled to analog-to-digital converter 382 by a line 384, and to bus 348 by a line 380.

Detector 356 and its associated circuitry work as described above with respect to detector 302 and its associated circuitry. In particular, offset compensation circuit 360 reduces the DC component which is not otherwise eliminated by a baseline restoration circuit in preamplifier 358. Also, similar to half-wave rectifier 330, half-wave rectifier 374 eliminates any voltage undershoots on the voltage-encoded pulse signal generated by overlap compensation circuit 364 before transmitting the overlap compensated signal to logarithmic amplifier 378.

Data acquisition system 301 overcomes high-speed related signal distortion by use of offset compensation circuits 316 and 360, as well as half-wave rectifiers 330 and 374. Specifically, offset compensation circuits 316 and 360 reduce the DC component not eliminated by baseline-restoration circuits, and half-wave rectifiers 330 and 374 eliminate signal undershoots caused by signal alignment errors in overlap compensation operations. Because data acquisition system 301 includes these additional circuits, the integrity of the data ultimately received by computer 354 or sorting circuitry is significantly increased.

Figure 4:
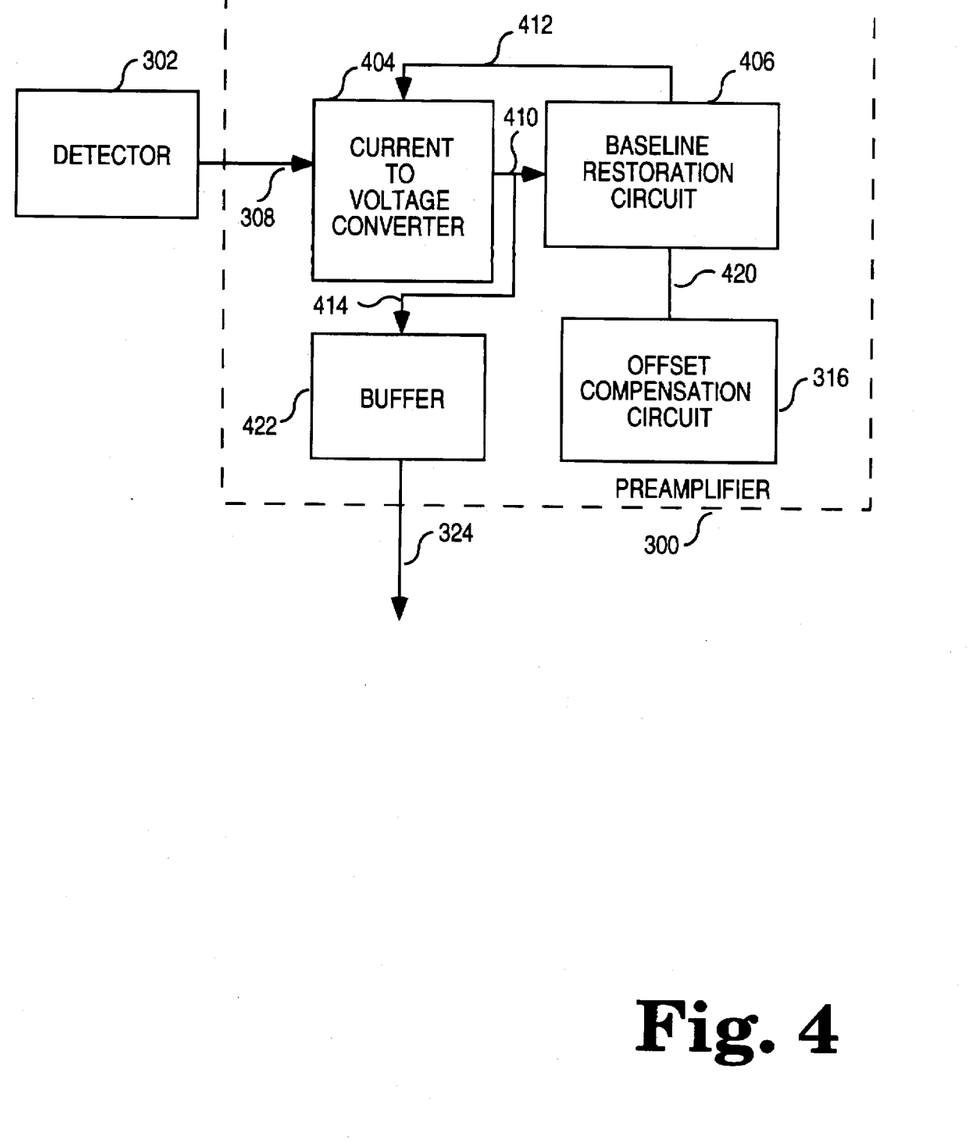
FIG. 4 is a block diagram illustrating a preamplifier with an offset compensation circuit according to an embodiment of the invention.

Referring now to FIG. 4, it illustrates preamplifier 300 in greater detail. Preamplifier 300 generally includes a current-to-voltage converter 404, a baseline restoration circuit 406, a signal buffer 422, and offset compensation circuit 316. Current-to-voltage converter 404 generates a voltage-encoded pulse signal over a line 410. The voltage level of voltage-encoded pulse signal varies responsive to the current of the current-encoded signal on coaxial cable 308. The voltage-encoded pulse signal is transmitted to baseline restoration circuit 406 over line 410.

Baseline restoration circuit 406 estimates the DC component of the signal on line 410. An estimated DC component signal is transmitted back to current-to-voltage converter 404 over a line 412. Current-to-voltage converter 404 then reduces the voltage-level encoded signal by the estimated DC component amount and transmits the compensated signal to signal buffer 422 over a line 414 for further processing.

As explained above, at high speed there is an inaccuracy between the signal on line 410 used to estimate the DC component, and the signal which is reduced by the DC component estimate. Consequently, the DC component would typically not be adequately reduced from the output signal on line 414. However, adjustable offset compensation circuit 316 is coupled to baseline restoration circuit 406 by a line 420. Adjustable offset compensation circuit 316 causes baseline restoration circuit 406 to alter (usually increase) the amplitude of the DC component estimate signal sent over line 412 by a predetermined amount. In the preferred embodiment, adjustable offset compensation circuit 316 increases the estimated DC component estimate signal on line 412 by an mount sufficient to more accurately reduce the DC component from the signal ultimately generated at line 414. From signal buffer 422, the DC compensated signal is then sent to overlap compensation circuit 326 as described above.

Figure 5:
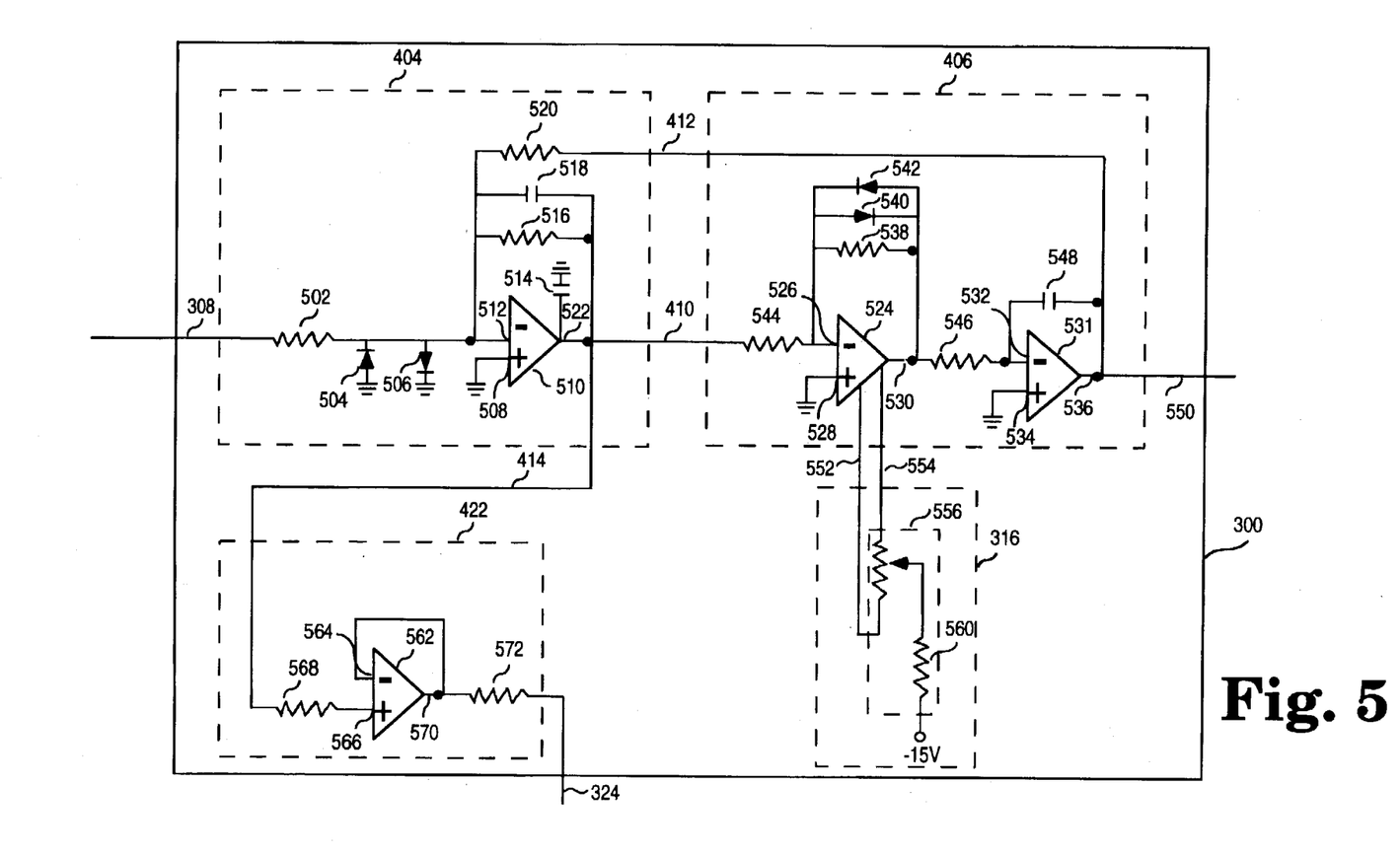
FIG. 5 is a schematic diagram illustrating the preamplifier of FIG. 4 in greater detail.

Referring to FIG. 5, it is a schematic diagram illustrating one embodiment of preamplifier 300. In the illustrated embodiment, current-to-voltage converter 404 includes a operational amplifier 510 with an output 522 and two inputs 508 and 512. Input 512 of operational amplifier 510 is coupled to coaxial cable 308 through a input protection resistor 502. Input 512 of operational amplifier 510 is coupled to ground through protection diode 504, to ground through diode 506, to the output 522 of operational amplifier 510 through a resistor 516, to the output 522 through a bandwidth limiting capacitor 518, and to line 412 through a resistor 520. Input 508 of operational amplifier 510 is coupled to ground. Operational amplifier 510 is also coupled to ground through a compensation capacitor 514. Through this arrangement of components, current-to-voltage converter 404 generates a signal on line 414 that has a voltage which varies in response to the current on coaxial cable 308. The voltage level on line 414 has been reduced responsive to the DC component estimate signal on line 412 and by offset compensation circuit 316 to reduce the DC component from the signal.

Baseline restoration circuit 406 generates the DC-offset estimate signal on line 412 in response to the voltage encoded signal on line 410 and a signal from adjustable offset compensation circuit 316. Baseline restoration circuit 406 includes a operational amplifier 524 with two inputs 526 and 528 and an output 530. Baseline restoration circuit 406 also includes a differential integrator 531 with two inputs 532 and 534 and an output 536. Input 526 of operational amplifier 524 is coupled to the output 530 of operational amplifier 524 through a resistor 538, through a diode 540, and through a diode 542. Input 526 of operational amplifier 524 is also coupled to line 410 through a resistor 544. Input 528 of operational amplifier 524 is coupled to ground. Output 530 of operational amplifier 524 is coupled to input 532 of differential integrator 531 through a resistor 546. Input 532 of differential integrator 531 is also coupled to output 536 of differential integrator 531 through a capacitor 548. Configured as described above, these components of baseline restoration circuit generate a signal over line 412 that has a voltage level equal to the estimated DC component of the voltage encoded signal on line 410. However, due to the limitations at higher pulse input rates between the signal adjusted based upon the signal on line 412 and the signal on line 410 from which the signal on line 412 is generated, baseline restoration circuit 406 must be adjusted by adjustable offset compensation circuit 316 to more accurately reduce the DC component from the signal generated on line 414.

Adjustable offset compensation circuit 316 is connected to "offset null" provision of operational amplifier 524 in baseline restoration circuit 406 by a plurality of lines 552 and 554. Adjustable offset compensation circuit 316 includes a potentiometer 556 which includes a resistor 560. The signal sent from potentiometer 556 to baseline restoration circuit 406 causes the voltage level of the DC-offset estimate signal on line 412 to be altered by an amount based on the setting of potentiometer 556. Preferably, potentiometer 556 is set to a level that will alter the DC-offset estimate signal on line 412 enough to more accurately reduce the DC component from the signal generated over line 324.

Signal buffer 422 buffers the signal on line 414 and drives the signal to overlap compensation circuit 326 via line 324. Signal buffer 422 includes a operational amplifier 562 with two inputs 564 and 566 and output 570. Input 564 is coupled to output 570. Input 566 is coupled to line 414 through a resistor 568. Output 570 is coupled to line 324 through a resistor 572.

In certain situations, it may be desired to know the DC component portion of signals generated by detectors in a flow cytometry system. As explained above, an estimate of this component is generated by baseline restoration circuit 406 over line 412. Optionally, baseline restoration circuit 406 may send the DC-offset estimate signal over a line 550 for processing by other circuits in addition to current-to-voltage converter 440.

Figure 6:
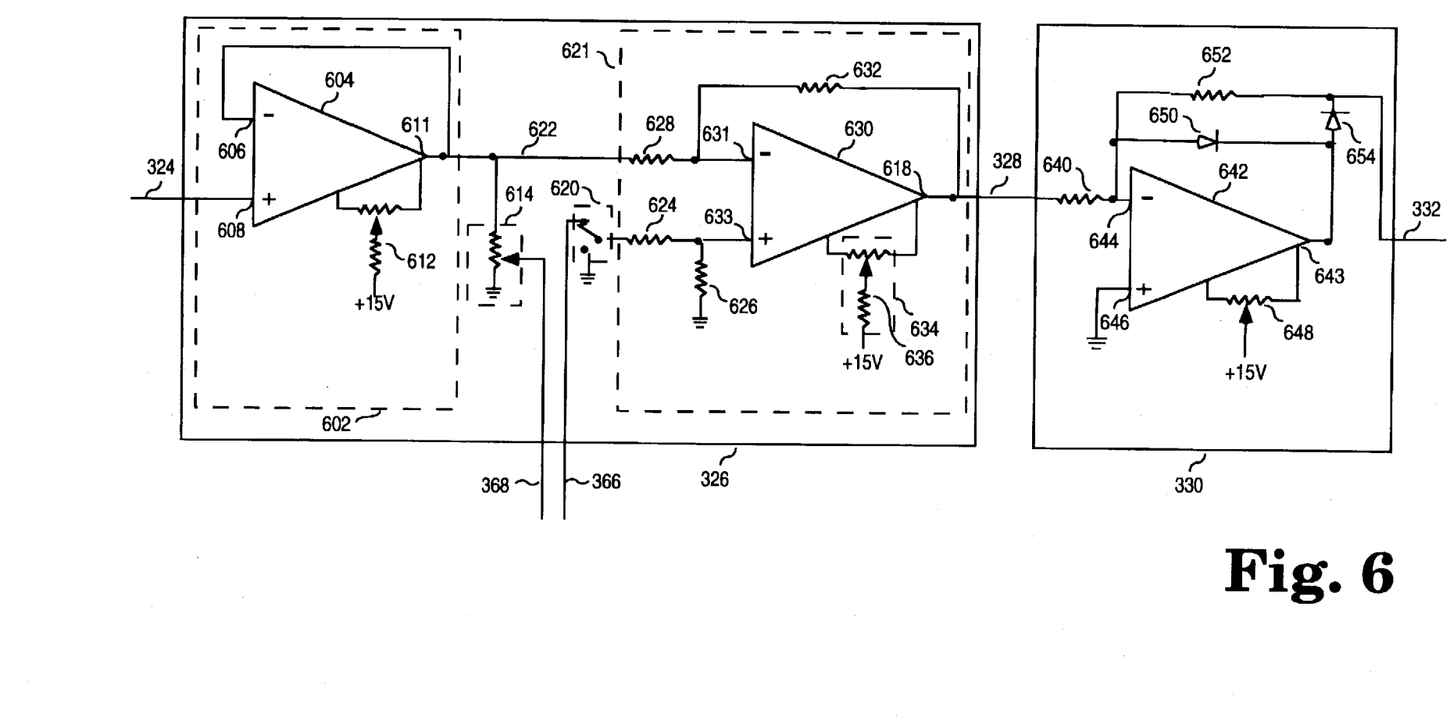
FIG. 6 is a schematic diagram illustrating an embodiment of the overlap compensation circuit and half-wave rectifier of FIG. 3.

Referring to FIG. 6, it is a schematic diagram illustrating overlap compensation circuit 326 and half-wave rectifier 330 of FIG. 3 in greater detail. Overlap compensation circuit 326 includes a buffer 602, a reduced signal transmission circuit 614, a switch 620, and a signal reduction circuit 621. Buffer 602 includes an operational amplifier 604 with two inputs 606 and 608 and an output 611. Input 608 of operational amplifier 604 is connected to line 324, and input 606 of operational amplifier 604 is connected to output 611 of operational amplifier 604. A potentiometer and a resistor 612 can be connected to a operational amplifier 604. The output 611 of operational amplifier 604 is coupled to signal subtraction circuit 621 by a line 622. Thus configured, buffer 602 buffers and drives the signal transmitted to overlap compensation circuit 326 by preamplifier 300 over line 324. The same result can be achieved by offset adjustment in the preamplifier.

Reduced signal transmission circuit 614 is connected to line 622. Reduced signal transmission circuit 614 is configured such that a percentage of the voltage on line 622 is transmitted to overlap compensation circuit 364 via line 368. The voltage on line 622 varies in response to the signal generated by detector 302. Detector 302 is configured to detect X-tagged particles. Detector 356 is configured to detect particles which are tagged differently than those detected by detector 302, which detects Y-tagged particles. However, even though detector 302 is configured to detect particles with a different type of tag, detector 302 may generate false detection indications because the light frequencies generated by the particles detectable by detector 356 partially overlap the frequencies emitted by the particles detectable by detector 302. As a result, the voltage on line 622 may increase when a Y-tagged particle passes by detector 302. To eliminate these false detection readings, signal reduction circuit 621 reduces the signal on line 622 with the signal on line 366. Overlap compensation circuit 364 subtracts the reduced signal on line 368 from a DC offset compensated signal from detector 356.

Line 366 carries a signal whose voltage is a percentage of the voltage-encoded pulse signal generated by preamplifier 358. Signal reduction circuit 621 includes a operational amplifier 630 with two inputs 631 and 633 and an output 618. Input 633 of operational amplifier 630 is connected to switch 620 through a resistor 624, and to ground through a resistor 626. Input 633 is coupled to line 366 through switch 620 when switch 620 is on, and is coupled to ground through switch 620 when switch 620 is off. Input 631 of operational amplifier 630 is coupled to line 622 through a resistor 628, and the output 618 of operational amplifier 630 through a resistor 632. An offset adjustment circuit 634, which includes a resistor 636, is also coupled to operational amplifier 630. When switch 620 is on, signal reduction circuit 621 generates a signal over line 328 based on the signal on line 622 subtracted by the signal on line 366.

Half-wave rectifier 330 generally includes a operational amplifier 642 with two inputs 644 and 646 and an output 643. Input 644 of operational amplifier 642 is coupled to line 328 through resistor 640, to line 322 through a resistor 652, and to the output 643 of operational amplifier 642 through a diode 650. Input 646 of operational amplifier 642 is coupled to ground. The output of operational amplifier 642 is coupled to line 332 through a diode 654. Operational amplifier 642 is also coupled to a potentiometer 648.

Half-wave rectifier 330 receives the signal on line 328 from overlap compensation circuit 326. The signal on line 328 coming from overlap compensation circuit 326 has a negative polarity. Half-wave rectifier 330 eliminates any above-zero voltage undershoots in the signal and transmits the resulting rectified signal over line 332. The rectified signal generated by half-wave rectifier 330 has a positive polarity.

As explained above, the signal reduction operation performed by signal reduction circuit 621 may result in signal spikes on line 328 above ground due to offset and analog component imprecision. Eliminating such above-zero signal undershoots by half-wave rectifier 330 will ensure that false signal spikes will not be present after the signal is log amplified by logarithmic amplifier 336.

The embodiments of preamplifier 300, overlap compensation circuit 326, and half-wave rectifier 330 described above with reference to FIGS. 5 and 6 may implemented with components having the operational parameters shown in Table 1. It should be understood that the values shown in Table 1, as well as the specific circuitry configurations described above, are merely exemplary. The invention may be implemented by a variety of circuitry configurations.

TABLE 1

| | |
|---|---|
| resistor 568 | 100 Ω |
| input protection resistor 502 | 200 Ω |
| protection diode 504 | Item 1N4148 available from Motorola |
| diode 506 | Item 1N4148 available from Motorola |
| operational amplifier 510 | Item AD829JN available from Analog Devices |
| compensation capacitor 514 | 4 pF |
| resistor 516 | 20K |
| capacitor 518 | 4 pF |
| resistor 520 | 20K |
| operational amplifier 524 | Item AD744JN available from Analog Devices |
| differential integrator 531 | Item AD744JN available from Analog Devices |
| resistor 538 | 100K |
| diode 540 | Item 1N4148 available from Motorola |
| resistor 544 | 1K |
| resistor 546 | 24.9K |
| capacitor 548 | 0.1 µF |
| potentiometer 556 | 2M |
| resistor 560 | 1M |
| operational amplifier 562 | Item AD847JN available from Analog Devices |
| resistor 572 | 100 Ω |
| operational amplifier 604 | Item AD845JN available from Analog Devices |
| resistor 612 | 392 Ω + 1K potentiometer |
| potentiometer 614 | 10K |
| resistor 624 | 10K |
| resistor 626 | 10K |
| resistor 628 | 10K |
| operational amplifier 630 | Item AD845JN available from Analog Devices |
| resistor 632 | 10K |
| potentiometer 634 | 1K |
| resistor 636 | 392 Ω + 1K potentiometer |
| resistor 640 | 1K |
| operational amplifier 642 | Item AD844AN available from Analog Devices |
| potentiometer 648 | 20K |
| diode 650 | Item HP5082-2810 available from Hewlett Packard |
| resistor 652 | 1K |
| diode 654 | Item HP5082-2810 available from Hewlett Packard |

Figure 7:
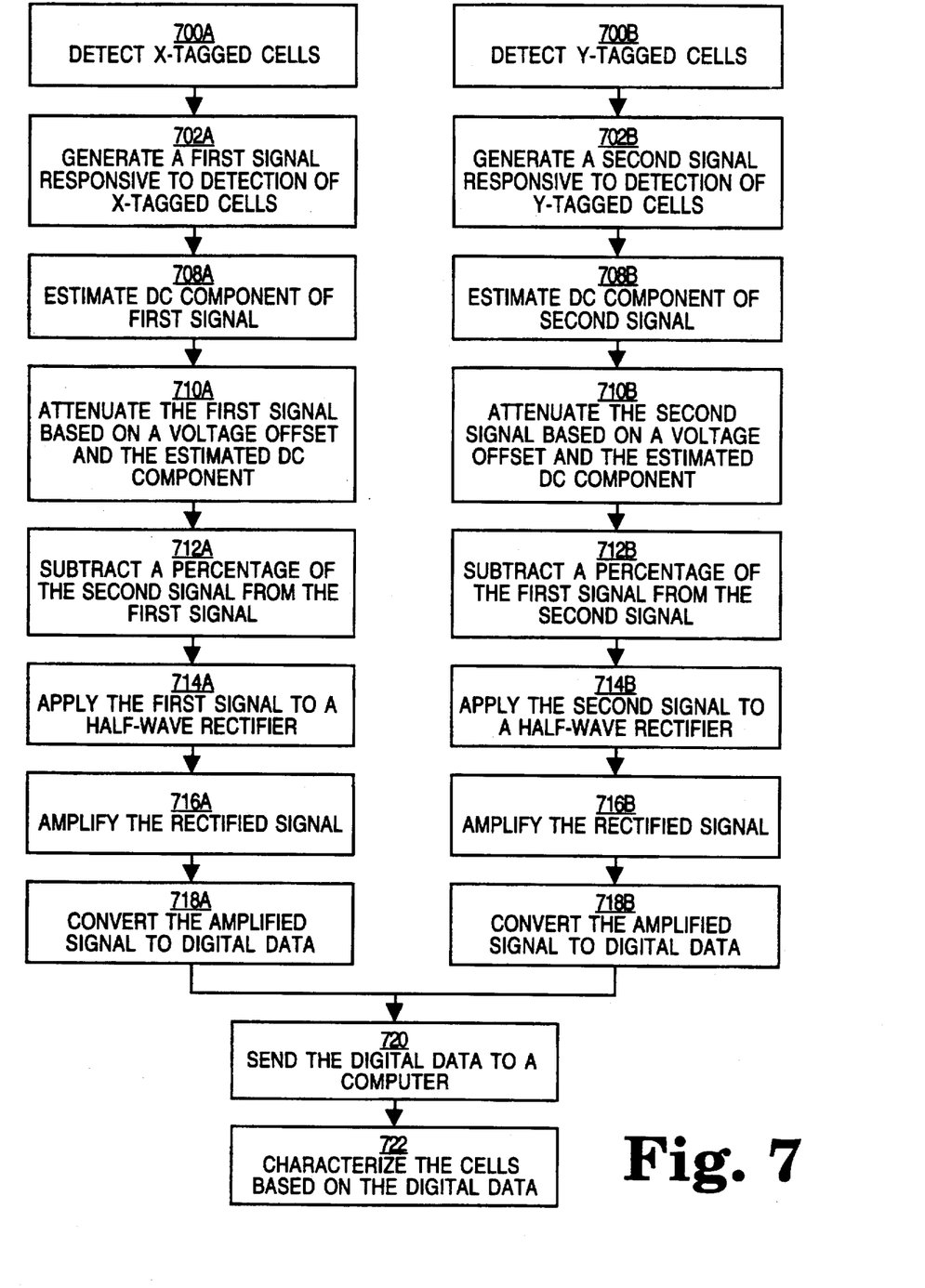
FIG. 7 is a flow chart illustrating the steps for acquiring data in multiple-detector high-speed flow cytometry system.

Referring now to FIG. 7, it is a flow chart illustrating a method for acquiring data to characterize particles in a flow cytometry system according to one embodiment of the invention. At step 700A, particles having a first tag type (e.g. X-tagged particles) are detected with a first detector. At step 702A, a first signal is generated responsive to detection of X-tagged particles. In the preferred embodiment, the first signal is a current-encoded signal.

At step 708A, the DC component of the first signal is estimated based on the first signal. Because the method is for use with high-speed data acquisition, a feedback circuit will typically underestimate the DC component. Therefore, at step 710A, the first signal is DC compensated based on a voltage offset summed with the estimated DC component. The voltage offset is adjustable.

A second signal is generated and processed concurrent with the generation and processing of the first signal. The second signal is a signal from a second detector that detects particles having a second tag type (e.g. Y-tagged particles). Specifically, at steps 700B and 702B, a second signal is generated responsive to detection Y-tagged particles by the second detector, and at steps 708B and 710B the second signal is DC compensated based on a voltage offset summed with an estimated DC component.

At steps 712A and 712B, two overlap compensated signals are generated based on the first signal and the second signal. Specifically, at step 712A, a percentage of the second signal is subtracted from the first signal to produce a first overlap compensated signal. At step 712B, a percentage of the first signal is subtracted from the second signal to produce a second overlap compensated signal.

At steps 714A and 714B, the overlap compensated signals are applied to half-wave rectifiers. At steps 716A and 716B, the rectified signals are log amplified to produce amplified signals. At steps 718A and 718B, the amplified signals are converted to digital data. At step 720, the digital data is transmitted to a computer. Finally, at step 722, the particles are characterized based on the digital data.

In the multiple-detector system shown in FIG. 3, the circuits which process the signal from detector 356 include preamplifier 358 with offset compensation circuit 360, overlap compensation circuit 364 which compensates the signal from detector 356 by a percentage of the signal from detector 302, and half-wave rectifier 374 which eliminates any signal undershoots caused by the overlap compensation circuit due to timing and component imprecision.

Once stored in FIFO buffers 344 and 386, the digital data from detectors 302 and 356 are aligned so that the data from each detector for a given particle is sequentially placed on bus 348. Each particle may be characterized based on the signal generated by detectors 302 and 356 responsive to the signal. In a particle-sorting system, a sorting mechanism is activated to segregate the particles based on the determined characterization.

ELECTRONIC BENCH TESTS

The circuitry described above may be adjusted as follows. First, tie line 308 to ground. Connect a digital volt meter (DVM) with a minimum of 0.1 mV resolution to the output 611 of operational amplifier 604. Adjust offset compensation circuit 316 so that the DVM reads 0.0 V. Apply a Gaussian pulse shape of 2 microseconds length, 10 kHz frequency to lines 308 and 357. Adjust the amplitude of the pulse shape to measure 2 mV top-top at line 622 of overlap compensation circuit 326 and at the corresponding line of overlap compensation circuit 364. Set compensation adjustment to 100% by adjusting potentiometer 614 in overlap compensation circuit 326 and the corresponding potentiometer in overlap compensation circuit 364. Set switch 620 and the corresponding switch in overlap compensation circuit 364 to the "compensation on" position. Adjust potentiometer 634 so that output 328 measures 0.0 mV. Adjust the corresponding potentiometer in overlap compensation circuit 362 so that output 376 measures 0.0 mV.

The half-wave rectifier 330 may be adjusted using the same input signals to lines 308 and 357 as described above. Overlap compensation circuit 364 is adjusted so that the signal on line 366 is at 50%. View signal 332 on an oscilloscope. A positive 1 mV top-top pulse should be measured. Adjust potentiometer 648 when an offset is present so that 1 mV top—top pulse is measured with no offset. Use a similar method to adjust half-wave rectifier 374. Potentiometer 614 and the corresponding potentiometer in overlap compensation circuit 364 are set using calibration beads or samples.

While specific embodiments of the present invention have been described, various modifications and substitutions will become apparent by this disclosure. For example, DC offset compensation has been described with respect to two fluorescence channels. However, the in invention is not limited to any particular number of channels and may readily be expanded to handle compensation between any number of channels. Such modifications and substitutions are within the scope of the present invention, and are intended to be covered by the following claims.

What is claimed is:

1. A preamplifier for use in a flow cytometry system, the preamplifier comprising:

a baseline restoration circuit coupled to receive a voltage-encoded signal, the baseline restoration circuit generating an estimated DC component responsive to the voltage-encoded signal; and an offset compensation circuit coupled to the baseline restoration circuit, the offset compensation circuit generating an offset signal indicating a voltage offset; and wherein the preamplifier is configured to attenuate the voltage-encoded signal based on the voltage offset and the estimated DC component to produce a DC compensated signal.

2. The preamplifier of claim 1 wherein:

the baseline restoration circuit generates a DC component signal having a voltage level equal to the offset signal summed with the estimated DC component; and the DC compensated signal is generated by attenuating the voltage-encoded signal based on the DC component signal.

3. The preamplifier of claim 1 wherein said offset compensation circuit includes an offset compensation level adjustment mechanism that allows a user to set the voltage offset indicated by said offset signal.

4. The preamplifier of claim 3 wherein said offset compensation level adjustment mechanism includes a potentiometer.

5. A data acquisition system comprising a preamplifier as recited in claim 1, the data acquisition system further comprising:

a detector disposed to detect particles having a first tag type, the detector generating an analog current which varies responsive to detecting particles having the first tag type;

a current-to-voltage converter coupled to the detector, the current-to-voltage converter receiving the analog current from said detector and generating the voltage-encoded signal responsive to the analog current;

an amplifier coupled to the preamplifier, the amplifier amplifying the DC compensated signal and generating an amplified signal;

an analog-to-digital converter coupled to the amplifier, the analog-to-digital converter generating digital data responsive to the amplified signal; and a computer coupled to the analog-to-digital converter, the computer categorizing the particles responsive to the digital data.

6. The data acquisition system of claim 5 wherein said particles are cells.

7. A data acquisition system comprising:

a detector disposed to detect particles having a first tag type, the detector generating an analog current which varies responsive to detecting particles having the first tag type;

a current-to-voltage converter coupled to the detector, the current-to-voltage converter receiving the analog current from said detector and generating the voltage-encoded signal responsive to the analog current;

a preamplifier comprising:
- a baseline restoration circuit coupled to receive a voltage-encoded signal, the baseline restoration circuit generating an estimated DC component responsive to the voltage-encoded signal; and
- an offset compensation circuit coupled to the baseline restoration circuit, the offset compensation circuit generating an offset signal indicating a voltage offset; and
- wherein the preamplifier is configured to attenuate the voltage-encoded signal based on the voltage offset and the estimated DC component to produce a DC compensated signal;

an amplifier coupled to the preamplifier, the amplifier amplifying the DC compensated signal and generating an amplified signal;

an analog-to-digital converter coupled to the amplifier, the analog-to-digital converter generating digital data responsive to the amplified signal;

a computer coupled to the analog-to-digital converter, the computer categorizing the particles responsive to the digital data;

a second detector disposed to detect particles having a second tag type, the second detector generating a second analog current which varies responsive to detecting particles having the second tag type;

a reduced signal transmission circuit coupled to the second detector, the reduced signal transmission circuit receiving the second analog current and generating a reduced level signal, the reduced level signal being the second analog current reduced by a percentage;

an overlap compensation circuit coupled between the preamplifier and the amplifier, the overlap compensation circuit being coupled to the reduced signal transmission circuit, the overlap compensation circuit subtracting the reduced level signal from the DC compensated signal to produce an overlap compensated signal; and a half-wave rectifier coupled between the overlap compensation circuit and the amplifier, the half-wave rectifier receiving the overlap compensated signal and generating a rectified signal, the amplifier amplifying the rectified signal to produce the amplified signal.

8. A spectral overlap compensation system for use in a flow cytometry system, the spectral overlap compensation system comprising:

an overlap compensation circuit coupled to a first detector, said overlap compensation circuit receiving a first signal from said first detector, the overlap compensation circuit subtracting a second signal from the first signal to produce an overlap compensated signal, wherein the second signal is based on signals produced by one or more second detectors;

a half-wave rectifier coupled to the overlap compensation circuit, the half-wave rectifier receiving the overlap compensated signal and generating a rectified signal; and an amplifier coupled to the half-wave rectifier, the amplifier amplifying the rectified signal and generating an amplified signal.

9. The spectral overlap compensation circuit of claim 8 wherein said amplifier is a logarithmic amplifier configured to generate said amplified signal based on the absolute value of said overlap compensated signal.

10. The spectral overlap compensation system of claim 8 wherein said overlap compensation circuit is coupled to said first detector through a preamplifier circuit, wherein said preamplifier circuit includes:
- a current-to-voltage converter coupled to the first detector, the current-to-voltage converter receiving an analog current from said first detector and generating a voltage-encoded signal responsive to the analog current;
- a baseline restoration circuit coupled to the current-to-voltage converter, the baseline restoration circuit generating an estimated DC component responsive to the voltage-encoded signal;
- an offset compensation circuit coupled to the baseline restoration circuit, the offset compensation circuit generating an offset signal indicating a voltage offset; and
- the preamplifier circuit being configured to attenuate the voltage-encoded signal based on the voltage offset and the estimated DC component to produce said first signal.

11. A data acquisition system that includes a spectral overlap compensation system as recited in claim 8, the data acquisition system further comprising:

said first detector disposed to detect particles having a first tag type, the first detector generating a first analog current which varies responsive to detecting particles having the first tag type, wherein said first signal is based on said first analog current;

a second detector disposed to detect particles having a second tag type, the second detector generating a second analog current which varies responsive to detecting particles having the second tag type;

a reduced signal transmission circuit coupled to the second detector, the reduced signal transmission circuit receiving the second analog current and generating said second signal, the second signal representing the second analog current reduced by a percentage;

an analog-to-digital converter coupled to the amplifier, the analog-to-digital converter generating digital data responsive to the amplified signal; and a computer coupled to the analog-to-digital converter, the computer categorizing the particles responsive to the digital data.

12. The data acquisition system of claim 11 further comprising a preamplifier coupled between the first detector and the overlap compensation circuit, the preamplifier receiving the first analog current from the first detector, the preamplifier generating a voltage-encoded signal responsive to said first analog current, the preamplifier generating an estimated DC component of the voltage-encoded signal, the preamplifier attenuating the voltage-encoded signal based on a voltage offset and the estimated DC component to produce a DC compensated signal, the overlap compensation circuit generating the overlap compensated signal by subtracting the second signal from the DC compensated signal.

13. The data acquisition system of claim 12 wherein the preamplifier includes:
a current-to-voltage converter coupled to the first detector, the current-to-voltage converter receiving the first analog current and generating the voltage-encoded signal responsive to the analog current;

a baseline restoration circuit coupled to the current-to-voltage converter, the baseline restoration circuit estimating the estimated DC component responsive to the voltage-encoded signal; and an offset compensation circuit coupled to the baseline restoration circuit, the offset compensation circuit generating an offset signal indicating the voltage offset.

14. The data acquisition system of claim 13 wherein:

the baseline restoration circuit generates a DC component signal having a voltage level equal to the offset signal summed with the estimated DC component; and the DC compensated signal is generated by attenuating the voltage-encoded signal based on the DC component signal.

15. The data acquisition system of claim 11 wherein said particles are cells.

16. A data acquisition system for use in a flow cytometry system, comprising:

a first detector disposed to detect particles having a first tag type, the first detector generating a first analog current which varies responsive to detecting particles having the first tag type;

a first preamplifier coupled to the first detector, the first preamplifier receiving the first analog current from the first detector, the first preamplifier estimating a first estimated DC component of the first analog current based on the first analog current, the first preamplifier attenuating the first analog current based on a first voltage offset and the first estimated DC component to produce a first DC compensated signal;

a first overlap compensation circuit, the first overlap compensation circuit including a first reduced signal transmission circuit coupled to the first preamplifier, the first reduced signal transmission circuit receiving the first DC compensated signal and generating a first reduced level signal, the first reduced level signal being the first DC compensated signal reduced by a first percentage, and a first subtraction circuit coupled to the first preamplifier, the first subtraction circuit subtracting a second reduced level signal from the first DC compensated signal to produce a first overlap compensated signal;

a first half-wave rectifier coupled to the first overlap compensation circuit, the first half-wave rectifier receiving the first overlap compensated signal and generating a first rectified signal;

a first amplifier coupled to the first half-wave rectifier, the first amplifier amplifying the first rectified signal to generate a first amplified signal;

a first analog-to-digital converter coupled to the first amplifier, the first analog-to-digital converter generating digital data responsive to the first amplified signal;

a second detector disposed to detect particles having a second tag type, the second detector generating a second analog current which varies responsive to detecting particles having the second tag type;

a second preamplifier coupled to the second detector, the second preamplifier receiving the second analog current from the second detector, the second preamplifier estimating a second estimated DC component of the second analog current based on the second analog current, the second preamplifier Attenuating the second analog current based on a second voltage offset and the second estimated DC component to produce a second DC compensated signal;

a second overlap compensation circuit, the second overlap compensation circuit including a second reduced signal transmission circuit coupled to the second preamplifier and to the first subtraction circuit, the second reduced signal transmission circuit receiving the second DC compensated signal and generating the second reduced level signal, the second reduced level signal being the second DC compensated signal reduced by a second percentage, and a second subtraction circuit coupled to the second preamplifier and to the first reduced signal transmission circuit, the second subtraction circuit subtracting the first reduced level signal from the second DC compensated signal to produce a second overlap compensated signal;

a second half-wave rectifier coupled to the second overlap compensation circuit, the second half-wave rectifier receiving the second overlap compensated signal and generating a second rectified signal;

a second amplifier coupled to the second half-wave rectifier, the second amplifier amplifying the second rectified signal to generate a second amplified signal;

a second analog-to-digital converter coupled to the second amplifier, the second analog-to-digital converter generating digital data responsive to the second amplified signal;

a computer coupled to the first analog-to-digital converter and to the second analog-to-digital converter, the computer categorizing the particles responsive to the digital data generated by the first analog-to-digital converter and the second analog-to-digital converter.

17. A method for acquiring data to characterize particles in a flow cytometry system, the method comprising the steps of:

detecting particles having a first tag type with a first detector;

generating a first signal responsive to detection of particles having the first tag type by the first detector;

detecting particles having a second tag type with a second detector;

generating a second signal responsive to detection of particles having the second tag type by the second detector;

subtracting a percentage of the second signal from the first signal to produce an overlap compensated signal;

applying the overlap compensated signal to a half-wave rectifier to produce a rectified signal;

amplifying the rectified signal to produce an amplified signal;

converting the amplified signal to digital data;

transmitting the digital data to a computer;

causing the computer to characterize particles based on the digital data.

18. The method of claim 17 farther including the steps of:

estimating an estimated DC component of the first signal;

attenuating the first signal based on a predetermined voltage offset summed with the estimated DC component prior to subtracting the percentage of the second signal from the first signal to produce the overlap compensated signal.

19. A method for performing spectral overlap compensation in a high-speed flow cytometry system, comprising the steps of:

receiving a first signal from a first detector configured to detect signals from a first tag type;

receiving a second signal from a second detector configured to detect signals from a second tag type;

subtracting a percentage of the second signal from the first signal to produce an overlap-compensated signal; and rectifying the overlap-compensated signal to eliminate any undershoot caused during said step of subtracting.

20. The method of claim 19 wherein said step of receiving said first signal includes:

receiving an analog current from said first detector;

converting said analog current into a voltage-encoded signal;

generating an estimated DC component of said voltage-encoded signal; and attenuating the voltage-encoded signal based on a voltage offset summed with the estimated DC component to produce said first signal.

21. The method of claim 19 wherein said flow cytometry system has a pulse rise time of no more than approximately two microseconds.

* * * * *

UNITED STATES PATENT AND TRADEMARK OFFICE
CERTIFICATE OF CORRECTION

PATENT NO.    : 5,675,517
DATED         : October 7, 1997
INVENTOR(S)   : Willem Stokijk It is certified that error appears in the above-identified patent and that said Letters Patent is hereby corrected as shown below:

In column 7 at line 46 delete "mount" and insert --amount--

Signed and Sealed this

Twenty-third Day of December, 1997

Attest:

BRUCE LEHMAN

Attesting Officer          Commissioner of Patents and Trademarks